(12) United States Patent
Burkert

(10) Patent No.: US 10,203,273 B2
(45) Date of Patent: Feb. 12, 2019

(54) METHOD OF STERILIZING AND TESTING THE INTEGRITY OF DIALYZERS

(71) Applicant: B. BRAUN AVITUM AG, Melsungen (DE)

(72) Inventor: Sina Burkert, Dresden (DE)

(73) Assignee: B. BRAUN AVITUM AG, Melsungen (DE)

( * ) Notice: Subject to any disclaimer, the term of this patent is extended or adjusted under 35 U.S.C. 154(b) by 82 days.

(21) Appl. No.: 15/333,562

(22) Filed: Oct. 25, 2016

(65) Prior Publication Data
US 2017/0138833 A1   May 18, 2017

(30) Foreign Application Priority Data
Nov. 18, 2015   (DE) .......................... 10 2015 120 003

(51) Int. Cl.
| | | |
|---|---|---|
| G01N 15/08 | (2006.01) | |
| A61L 2/18 | (2006.01) | |
| B01D 65/02 | (2006.01) | |
| B01D 65/10 | (2006.01) | |
| A61M 1/16 | (2006.01) | |
| B01D 61/30 | (2006.01) | |
| B01D 63/02 | (2006.01) | |

(52) U.S. Cl.
CPC .............. *G01N 15/082* (2013.01); *A61L 2/18* (2013.01); *A61L 2/183* (2013.01); *A61L 2/186* (2013.01); *A61M 1/169* (2013.01); *A61M 1/1682* (2014.02); *A61M 1/1684* (2014.02); *B01D 61/30* (2013.01); *B01D 63/02* (2013.01); *B01D 65/022* (2013.01); *B01D 65/102* (2013.01); *A61L 2202/15* (2013.01); *A61L 2202/24* (2013.01); *A61M 2205/705* (2013.01); *A61M 2207/00* (2013.01); *B01D 2201/085* (2013.01); *B01D 2321/168* (2013.01); *G01N 2015/084* (2013.01)

(58) Field of Classification Search
CPC . A61L 2/18; A61L 2/183; A61L 2/186; A61L 2202/15; A61M 1/1682; A61M 1/1684; A61M 1/169; A61M 2202/24; A61M 2205/705; A61M 2207/00; B01D 61/30; B01D 63/02; B01D 65/022; B01D 65/102; B01D 2201/085; B01D 2321/168; G01N 15/082; G01N 2015/084
See application file for complete search history.

(56) References Cited

U.S. PATENT DOCUMENTS

| | | | | |
|---|---|---|---|---|
| 4,148,606 | A * | 4/1979 | Morita | A61L 2/18 422/23 |
| 4,209,402 | A * | 6/1980 | Gentles | B01D 65/02 134/95.1 |
| 4,695,385 | A | 9/1987 | Boag | |
| 5,252,213 | A | 10/1993 | Ahmad et al. | |
| 5,498,338 | A * | 3/1996 | Kruger | A61M 1/28 210/259 |
| 5,594,161 | A | 1/1997 | Randhahn et al. | |
| 5,628,959 | A | 5/1997 | Kross | |
| 5,808,181 | A | 9/1998 | Wamsiedler et al. | |
| 5,900,270 | A * | 5/1999 | Smith, III | B01D 65/102 324/439 |
| 6,568,282 | B1 * | 5/2003 | Ganzi | B01D 65/102 73/38 |
| 6,758,975 | B2 * | 7/2004 | Peabody | A61L 2/022 210/257.2 |
| 8,562,908 | B2 * | 10/2013 | Kenley | A61L 2/186 422/44 |
| 2002/0162778 | A1 * | 11/2002 | Peabody | A61L 2/022 210/85 |
| 2013/0037485 | A1 * | 2/2013 | Wilt | A61M 1/1037 210/646 |

FOREIGN PATENT DOCUMENTS

| | | | |
|---|---|---|---|
| DE | 38 05 361 | 9/1988 | |
| DE | 10 2006 051 656 | 5/2008 | |
| DE | 19655227 B4 * | 8/2009 | .............. A61L 2/04 |
| DE | 19655227 B4 | 8/2009 | |
| EP | 0035405 A2 | 9/1981 | |
| JP | 2002186666 A * | 7/2002 | |
| JP | 2004285154 A * | 10/2004 | |

(Continued)

OTHER PUBLICATIONS

Rutala et al., "Guidelines for Disinfection and Sterilization in Healthcare Facilities, 2008", Centers for Disease Control, Feb. 15, 2017.*
German Search Report for DE 10 2015 210 003.1 dated Jun. 15, 2016, with translation.
Extended European Search Report for European Application No. 16 197 526.3, dated Mar. 30, 2017, including English translation, 15 pages.

(Continued)

*Primary Examiner* — David A Rogers
(74) *Attorney, Agent, or Firm* — RatnerPrestia

(57) ABSTRACT

Methods of combined sterilization and integrity testing of dialyzers such as hollow fiber dialyzers are disclosed. Sterilization and integrity testing may be performed by treating the dialyzer with a sterilization fluid for sterilizing at least the blood-side compartment of the dialyzer and for wetting the dialysis membrane of the dialyzer with the sterilization fluid, and carrying out an integrity testing of the dialysis membrane wetted with the sterilization fluid, wherein the sterilization fluid is selected from aqueous solutions containing peroxide and/or ozone, the peroxide being selected from peroxides which disintegrate into water, oxygen and/or volatile organic compounds, and from aqueous solutions containing chlorine, bromine and/or iodine.

13 Claims, No Drawings

(56) References Cited

FOREIGN PATENT DOCUMENTS

WO     WO 2012/020048     2/2012
WO     WO 2014/128306     8/2014

OTHER PUBLICATIONS

Cardiovascular Implants and Extracorporeal Systems—Hemodialysers, Haemodiazers, Hemofilters and Hemoconcentrators, dated Mar. 2014 (DIN EN ISO 8637), p. 11 of 30 pages.
Sterilization of Health Care Products—Radiation—Part 1: Requirements for development, validation and routine control of a sterilization process for medical devices, dated Dec. 2013, (DIN EN ISO 11137-1), pp. 16-24.

\* cited by examiner

METHOD OF STERILIZING AND TESTING THE INTEGRITY OF DIALYZERS

CROSS REFERENCE TO RELATED APPLICATIONS

This application claims priority to German application DE 10 2015 120 003.1 filed Nov. 18, 2015, the contents of such application being incorporated by reference herein.

FIELD OF THE INVENTION

The present invention relates to a method of sterilizing and testing the integrity of dialyzers.

BACKGROUND OF THE INVENTION

Functional testing and sterilization of medical apparatuses are essential prerequisites for ensuring optimum care of patients and for preventing infectious pathogens from being transmitted to the patient.

In the dialyzers used in today's modern medicine for hemodialysis and hemo(dia)filtration, especially hollow fiber dialyzers, in which the hollow fibers through which blood is flowing form the filter membrane the integrity testing and the sterilization are carried out in plural steps independent of each other.

In a hollow fiber dialyzer, in the course of the manufacturing process after the process steps of inserting the fiber bundle into the dialyzer housing, sealing of fibers and mounting of blood caps, during a first testing step at first the tightness of the fibers is tested.

DESCRIPTION OF THE RELATED ART

For this purpose, the dialyzer is usually rinsed during a wet leak test at first with distilled or deionized water, especially with water deionized by reverse osmosis (RO water) and is subjected to an integrity test, for example a bubble-point test or a diffusion test, so as to determine the tightness of the hollow fibers. An integrity testing is an essential part of EN ISO 8637:2014, Section 4.4.2 Integrity of the blood area. Methods of testing the integrity of dialyzer membranes are described, for example, in U.S. Pat. No. 5,594,161 A1 and WO 2012/020048 A1.

If the dialyzer passes the test, the water is removed, by heating, for example by microwave drying with subsequent drying by hot air previously purified through sterile filter.

Since drying is carried out at temperatures of no more than approximately 100° C. which are not sufficient for sterilizing the dialyzer, the dialyzer is subsequently subjected to a separate sterilization process so as to kill pathogenic germs and spores.

WO 2014/128306 describes a testing and drying device for functional testing of dialyzers. For wet leak testing by said devices, on the dialysis solution side water can flow through the dialyzer through ports for air and liquid medium and on the blood side dry air can flow through the same, wherein the tightness of the fibers is tested. After that, air drying of the dialyzer is carried out through said ports. After the functional testing and further drying the dialyzer has to be subjected to a subsequent sterilization process.

Methods and apparatuses for drying dialyzers with microwave drying are known from DE 10 2006 051 656 A1, for example. In this case, too, after drying the dialyzer has to be subjected to a subsequent sterilization process.

In the state of the art, the sterilization of dialyzers is carried out either chemically by sterilization with ethylenoxide (EtO) or formalin solution or by radiosterilization, especially gamma radiation, wherein the bioburden requirements under EN ISO 11137-2013 (D) have to be met. However, the chemical sterilization methods show the drawback that after sterilization toxic residues which have to be removed by careful rinsing prior to using the dialyzer remain within the dialyzer.

Radiosterilization of the dialyzer is typically not performed by the manufacturer but by an independent service provider and in any case has the drawback of great logistic efforts being required. Another drawback of radiosterilization consists in the load of the materials induced by radiation, e.g. degradation of the materials as well as formation of possible toxic components. For sterilizing blood hose systems also the sterilization using hydrogen peroxide plasma is known, which is not used for sterilizing dialyzers, however.

The known methods of testing the integrity of dialyzers in connection with chemical sterilization methods or radiosterilization are time-consuming and expensive.

Therefore, it object of the present invention to provide a simple and inexpensive method of sterilizing and testing the integrity of dialyzers, for example hollow fiber dialyzers.

This object is achieved by the method according to the independent claim comprising the following steps of:
  a) treating the dialyzer with a sterilization fluid for sterilizing at least the blood-side compartment of the dialyzer and for wetting the dialysis membrane of the dialyzer with the sterilization fluid; and
  b) carrying out an integrity testing of the dialysis membrane wetted with the sterilization fluid,
wherein the sterilization fluid is selected from:
  (i) aqueous solutions containing peroxide and/or ozone, with the peroxide being selected from peroxides which disintegrate into water, oxygen and/or volatile organic compounds; and/or
  (ii) aqueous solutions containing chlorine, bromine and/or iodine.

Further embodiments of the method according to, aspects of the invention are described in the subclaims.

The sterilization fluids made use of according, to aspects of the invention are not only suited for sterilizing the dialyzer but may also be employed for preparing and implementing the functional testing. In this way the dialyzer be tested, in combination with the sterilization, for integrity, especially tightness, of the dialysis membrane, for example of the hollow fibers.

In accordance with the invention, aqueous solutions of peroxides and/or ozone and/or aqueous solutions of chlorine, bromine and/or iodine may be used as sterilization fluid.

As peroxides those peroxides are suited which at ambient temperature or at elevated temperatures disintegrate into water, oxygen and/or volatile organic compounds and in this way can escape in gaseous form and free of residues through a dialysis membrane such as a hollow fiber membrane. Volatile organic compounds are accordingly meant to be organic compounds which at normal pressure have a boiling point of up to 120° C.

Of advantage, the peroxide-containing aqueous solution used as sterilization fluid contains peroxides of the formula $R^1$—O—O—$R^2$, wherein $R^1$ and $R^2$ independently of each other are H, $CH_3$, $C_2H_5$ and $CH_3C(O)$ as well as mixtures thereof. Suitable peroxides are, for example, hydrogen peroxide ($H_2O_2$), methyl hydroperoxide ($CH_3OOH$), ethyl hydroperoxide ($C_2H_5OOH$), dimethyl peroxide (($CH_3)_2O_2$), diethyl peroxide (($C_2H_5)_2O_2$), ethyl methyl peroxide ($C_2H_5OOCH_3$), peroxy acetic acid ($H_3CC(O)O$—OH) and mixtures thereof. Especially preferred are aqueous hydrogen peroxide solutions, wherein hydrogen peroxide in solution may be provided alone or else together with peroxy acetic acid or ozone. As regards aspects of labor law and environmental protection law during production, hydrogen peroxide solutions constitute the preferred choice.

Commercial peroxide solutions may be used as aqueous peroxide solutions. Suitable peroxide solutions are, except for peracid solutions, at least 3%, for example 3 to 35% peroxide solutions. Advantageously 5 to 30% peroxide solutions, of preference 5 to 28% peroxide solutions, and especially preferred 5 to 25% peroxide solutions, especially hydrogen peroxide solutions, are used. As peroxy acetic acid solutions expediently 0.1 to 0.5% solutions, preferably 0.15 to 0.35% solutions are used. Optionally peroxide solutions such as hydrogen peroxide solutions containing small amounts, for example 0.15 to 0.3%, of peroxy acetic acid may be used. The pH value of the aqueous peroxide solutions usually is within the acid range, advantageously within the range of 2.0 to 6.5, especially within the range of 3.5 to 5.0.

Suitable aqueous ozone solutions exhibit an ozone content of 1 to 3 ppm of ozone, for example.

Aqueous solutions containing chlorine, bromine and/or iodine usually have a halogen content of 2% or more. Aqueous chlorine solutions are preferred.

Aqueous peroxide solutions, especially aqueous hydrogen peroxide solutions, with or without peroxy acetic acid, are particularly preferred, as a treatment with said solutions has a positive influence on the hemo-compatibility of the dialyzer surfaces.

The sterilization fluids used according to aspects of the invention are known to those skilled in the art and are commercially available. Suitable approved sterilization fluids are described, for example, in Rutala, W. A. et al., "Guideline for Disinfection and Sterilization in Healthcare Facilities, 2008" by Center of Disease Control (CDA).

Treatments of the dialyzer with the aqueous sterilization fluid for sterilizing the dialyzer and for wetting the membrane of the dialyzer and for testing the integrity of the membrane wetted with the sterilization fluid may be carried out during the manufacturing process and according to the method steps for integrity testing with water known to those skilled in the art.

In detail, the dialyzer is first made to contact the sterilization fluid at least on the side of the dialyzer exposed to the human blood (blood side). This can be done by filling and/or rinsing the dialyzer with the sterilization fluid. In accordance with the invention, it is sufficient to treat the blood side of the dialyzer with the sterilization fluid, as according to today's regulatory comprehension, it suffices when only the compartment exposed to the human blood is kept sterile. However, both the blood side and the dialysis solution side of the dialyzer may be treated with the sterilization fluid for the purpose of sterilization. In the case of a hollow fiber dialyzer, for sterilization and wetting the sterilization fluid is guided into the hollow fibers and optionally into the dialysis solution side compartment of the dialyzer.

The dialyzer is treated with the sterilization fluid in conditions in which at least the blood side of the dialyzer is sterilized. In the course or at the end of the sterilization process the membrane of the dialyzer, for example the hollow fiber membrane, is wetted with the sterilization fluid, for instance by pressing the sterilization fluid into the membrane so that the pores of the membrane are filled with the aqueous sterilization fluid. The conditions of sterilization are dependent on the respective sterilization fluid used, especially on the type and concentration of the sterilizing agent dissolved in the aqueous solution, for example of peroxide. Typically the time of the aqueous solutions used as sterilization fluid in accordance with the invention which is allowed to take effect on the dialyzer and the membrane amounts to at least 1 min and, for instance, is within the range of from 1 min to 10 h, advantageously within the range of from 1 min to 7.5 h. The treatment is usually carried out at a temperature ranging from 10 to 60° C., advantageously from 15 to 40° C., for example from 18 to 25° C. (ambient temperature). In general, the time allowed to take effect can be the shorter, the higher the concentration of the sterilization agent in the solution, the lower the pH of the solution and the higher the temperature. Hence the time allowed to take effect of the sterilization fluid in the case of a 7.5% aqueous hydrogen peroxide solution, for example, at a temperature ranging from 15 to 60° C. advantageously ranges from 1 min to 6 h and in the case of a 0.2% peroxy acetic acid solution advantageously ranges from 10 to 30 minutes.

After sterilization and wetting of the membrane, the sterilization fluid is removed from the blood compartment, for example by blowing out, and the dialyzer is subjected to functional testing in a known way in which the integrity, i.e. the tightness, of the wetted membrane, e.g. the hollow fiber membrane, is tested. For this purpose, the membrane wetted with the sterilization fluid is pressurized by a test gas such as air usually on one side, especially on the blood side, and after a stabilizing phase the integrity of the membrane can be tested in a known way by measuring the pressure drop after a predetermined period of time as compared to the initial pressure, for example after 10 s. The integrity may also be tested, for example, with bubble-point test or diffusion test or with known variants thereof. Methods and apparatuses for testing the integrity of membranes are described, for instance, in U.S. Pat. No. 5,594,161 A1 and WO 2012/020048 A1.

When the dialyzer has passed the integrity testing, optionally a drying step may follow in which the aqueous sterilization fluid is removed by heating and/or blowing out, for example. Drying may be carried out in a way known per se. Drying by heating is performed, as a rule, at temperatures of up to 110° C., usually up to 105° C. At said drying temperatures sterilization agents such as peroxides or ozone dissolved in the aqueous solution disintegrate into water, oxygen and/or volatile organic compounds which may escape, just as dissolved halogens, through the dialysis membrane, for example through the hollow fibers. According to an embodiment of the invention, the drying may comprise microwave drying, with subsequent drying by hot air previously purified by sterile filter, where necessary. For maintaining sterile conditions inlet and outlet closed by caps, for example. Methods and apparatuses for drying dialyzers, such as microwave drying, are known to those skilled in the art and are described, for example, in DE 10 2006 051 656 A1.

The method according to aspects of the invention allows a combined sterilization and integrity testing of dialyzers to be carried out using only one liquid medium. After drying no toxic residues will remain within the dialyzer so that no further rinsing operation is required prior to using the dialyzer. Moreover, sterilization and integrity testing can be carried out by the manufacturer so that both the costs and the logistic effort can be reduced. By the method according to aspects of the invention, proper hemo-compatibility of the dialyzer surfaces may be obtained, wherein no complete sterilization of the dialyzer is required, but it is also possible to sterilize merely the compartment of the dialyzer which is exposed to the blood.

The invention claimed is:

1. A method of sterilizing and testing the integrity of dialyzers, comprising the following steps of:
   a) treating a dialyzer with a sterilization fluid for sterilizing at least a blood-side compartment of the dialyzer and for wetting a dialysis membrane or hollow fiber membrane of the dialyzer with the sterilization fluid;
   b) removing the sterilization fluid from the blood-side compartment of the dialyzer, wherein the dialysis membrane or hollow fiber membrane of the dialyzer remains wetted with the sterilization fluid; and
   c) carrying out integrity testing of the dialysis membrane or hollow fiber membrane wetted with the sterilization fluid;
   wherein the sterilization fluid is selected from:
   (i) aqueous solutions containing peroxide and/or ozone, wherein the peroxide is selected from peroxides which disintegrate into water, oxygen and/or volatile organic compounds; and/or
   (ii) aqueous solutions containing chlorine, bromine and/or iodine.

2. The method according to claim 1, wherein the sterilization fluid is an aqueous solution of one or more peroxides of the formula $R^1$—O—O—$R^2$, with $R^1$ and $R^2$ being selected independently of each other from H, $CH_3$, $C_2H_5$ and $CH_3C(O)$.

3. The method according to claim 1, wherein the sterilization fluid is an aqueous solution of hydrogen peroxide ($H_2O_2$).

4. The method according to claim 3, wherein the aqueous solution of hydrogen peroxide is a 3% to 35% hydrogen peroxide solution.

5. The method according to claim 4, wherein the aqueous solution of hydrogen peroxide is a 6% to 25% hydrogen peroxide solution.

6. The method according to claim 3, wherein the hydrogen peroxide solution further contains peroxy acetic acid.

7. The method according to claim 1, wherein the sterilization is carried out at a temperature ranging from 15 to 60° C.

8. The method according to claim 1, wherein for testing the integrity of the dialysis membrane in step (b) the dialyzer is pressurized with a test gas on one side, and the integrity of the membrane is tested by measuring the pressure drop.

9. The method according to claim 8, wherein the one side is a blood side of the dialyzer.

10. The method according to claim 1, wherein the integrity of the dialysis membrane is tested in step (b) by means of a bubble-point test or diffusion test.

11. The method according to claim 1, wherein after the integrity testing in step (b) the method comprises the further step of:
    d) drying the dialyzer.

12. The method according to claim 1, wherein the dialyzer is a hollow fiber dialyzer.

13. The method according to claim 1, wherein the integrity of the dialysis membrane or hollow fiber membrane is tested by subjecting the dialysis membrane or hollow fiber membrane wetted with the sterilization fluid to a bubble-point test or diffusion test or by pressurizing the dialysis membrane or hollow fiber membrane wetted with the sterilization fluid on one side by a test gas and testing the integrity of the membrane by measuring the pressure drop.

* * * * *